United States Patent [19]

Song

[11] Patent Number: 5,834,032
[45] Date of Patent: Nov. 10, 1998

[54] COMPOSITIONS AND METHODS FOR TREATING DIABETES

[76] Inventor: Moon K. Song, 10922 Yolanda Ave., Northridge, Calif. 91326

[21] Appl. No.: 909,240

[22] Filed: Aug. 11, 1997

[51] Int. Cl.⁶ .......................... A61K 33/32; A61K 38/00
[52] U.S. Cl. ............................... 424/641; 514/9; 514/10; 514/400; 514/423; 514/866
[58] Field of Search ................... 514/9, 10, 400, 514/423, 866; 424/641

[56] References Cited

PUBLICATIONS

Mori et al.; Diabetes, vol. 37, Aug. 1988; pp. 1120–1122; *Cyclo (His–Pro) Concentration Changes in Brain Striatum of Hyperglycemic Rat*.

ICN, Inc.; *Alphabetical List of Products;* one page of catalog. 1998.

Prasad, Chandan; Peptides, vol. 16, No. 1, pp. 151–164; 1995; *Bioactive Cyclic Dipeptides*.

*Primary Examiner*—Leonard Schenkman
*Attorney, Agent, or Firm*—Knobbe Martens Olson & Bear, LLP

[57] ABSTRACT

Compositions and methods are useful for alleviating symptoms of diabetes in mammals. Some of the compositions include a zinc salt and cyclo-Hispro, and optionally contain arachidonic acid. Alternative compositions include a zinc salt, arachidonic acid and L-histidine. The compositions can be administered by oral route according to a daily regimen to result in decreased blood glucose concentrations.

23 Claims, No Drawings

COMPOSITIONS AND METHODS FOR TREATING DIABETES

FIELD OF THE INVENTION

The present invention relates to dietary supplementing compositions and methods useful for controlling the symptoms associated with diabetes. More particularly, the invention relates to compositions containing defined chemical species useful for treating diabetes, and methods based on administration of these compositions.

BACKGROUND OF THE INVENTION

Diabetes is one of the most common metabolic disorders in humans. Indeed, nearly 1 million Americans are afflicted with juvenile-onset diabetes. This form of the disease is also known as insulin-dependent or Type I diabetes, and usually appears abruptly during childhood or young adulthood. Type II, or non-insulin-dependent diabetes is characterized by a less abrupt onset. Type II diabetes commonly occurs beyond the age of 40 or so, and afflicts nearly 20 million Americans. Both types of diabetes impair the body's ability to access blood glucose for use as an energy source. Chronically high levels of blood sugar gradually damage many tissues and organs of the body.

Despite the availability of insulin treatment, diabetes remains a serious disease that is responsible for many deaths and substantial morbidity worldwide. For example, the life-span of the average diabetic is shortened by as much as 50%. Although insulin treatment can assist in regulating blood sugar levels, the degree of this control is typically insufficient to prevent many of the sequelae from diabetes. The consequences from long term diabetes can include eye damage, often leading to blindness; circulatory problems; problems with wound healing; and other serious consequences. Improved treatments for diabetes clearly are required.

Although it has been appreciated for many years that zinc deficiency is associated with reduced pancreatic insulin content (Huber et al., *J Nutr.* 103:1379 (1973)), decreased physiological potency of insulin (Boquist, *Acta Soc. Med. Upsal.* 72:358 (1967)), impaired glucose tolerance (Quarterman et al., *Br. J Nutr.* 28:75 (1972); Hendricks et al., *J Nutr.* 102:1079 (1972)) and increased insulin degradation, the correlation between zinc deficiency and the symptoms of diabetes has not been clearly established. In both diabetic animals and humans, plasma zinc levels are low (Levine et al., *Am. J Clin. Nutr.* 37:382 (1983); Chooi et al., *Nutr. Metab.* 20:135 (1976); Leu et al., *J Nutr.* 114:224 (1984); Rosner et al., *J Lab. Clin. Med.* 72:213 (1968)) and intestinal zinc absorption mechanisms are impaired (Kinlaw et al., *Am. J. Med.* 75:273 (1983); Gochishan et al., *Life Sci.* 32:1735 (1983); Johnson et al., *J. Nutr.* 115:1217 (1985); Kiilrich et al., *Clin. Chim. Acta.* 189:13 (1990); Song et al., *Life Sci.* 42:687 (1988)). These factors may aggravate the manifestation of diabetes based on the facts that zinc is involved in glucose transporter translocation from the cytosolic pool to membranes and expression of the human insulin receptor gene. Zinc also is known to be an integral component of nearly 300 metalloenzymes and proteins. Many of these enzymes are involved in the synthesis of insulin and the insulin receptor, as well as in glucose metabolism.

Previous studies have indicated that prostaglandins (PGs) and AA, a precursor of prostaglandins, chelate zinc and regulate intestinal zinc absorption and secretion (Song et al., *Am. J Physiol.* 234:E99 (1979); Song et al., *J Nutr.* 109:2151 (1979); Koletzko et al., *Eur. J Pediatr.* 143:310 (1985); Song et al., *Prost. Leuko. Med.* 17:159 (1984)). Isolated intestinal segments from diabetic rats showed significantly decreased intestinal zinc absorption capacity in Ussing chamber experiments (Song et al., *Life Sci.* 42:687 (1988)). When AA was added to the segment-bathing medium, zinc uptake increased significantly compared to controls. Although oral administration of low doses of AA decreased the intestinal zinc absorption rate, high doses of AA increased zinc absorption in non-diabetic rats (Song et al., *Prost. Leuko. Med.* 17:159 (1984)). The observations that the metabolism of both zinc and PG is altered in diabetic patients (Hurley et al., *Proc. Soc. Eptl. Biol. Med.* 123:692 (1966); Neggers et al., *Am. J Clin. Nutr.* 51:678 (1990); Pedersen et al., *Lancet* 1: 1124 (1964); Nasrat et al., *Diabetes Care* 14:553 (1991)) and that PGs regulate zinc metabolism suggested that zinc malnutrition may be linked to abnormal PG metabolism in diabetic animals and humans.

It has been reported that PGs and AA play important roles in the regulation of insulin release (Aalusha et al., "Prostaglandins and diabetes mellitus" in *Diabetes Mellitus, Theory and Practice*, ed. Ellenberg et al., pp. 295–308), and participate in numerous diabetes-related metabolic activities (Robertson, *Med. Clin.* 65:759 (1984); Katayama et al., *Hypertension* 7:554 (1985); Harrison et al., *Diabetologia* 18:65 (1980); Subbiah et al., *Biochem. Med.* 23:231 (1995); Johnson et al., *Lancet* 1:325 (1979); Shakir et al., *J. Clin. Invest.* 60:747 (1977); Goto et al., *Diabetes* 41:1644 (1992)).

Despite this background understanding, there still has not emerged an effective means of alleviating diabetic symptoms by purposefully manipulating zinc metabolism in diabetic animals. New compositions and methods that fill this need are disclosed herein.

SUMMARY OF THE INVENTION

One aspect of the present invention relates to a composition of matter that includes: (1) a zinc salt, which includes a zinc cation and an anion; (2) purified cyclo-Hispro; and (3) a pharmaceutically acceptable excipient, wherein the weight ratio of zinc cation to cyclo-Hispro in the composition is from about 1:10 to about 100:1. In one embodiment of the invented composition, the weight ratio of zinc cation to cyclo-Hispro is from about 1:6 to about 5:1. In another embodiment, the anion included in the zinc salt is an anion selected from the group consisting of chloride and sulfate. In still another embodiment, the invented composition additionally can include arachidonic acid. When arachidonic acid is included in the composition, the weight ratio of zinc cation to arachidonic acid is from about 1:200 to about 1:2. In addition to the zinc salt, the purified cyclo-Hispro and the pharmaceutically acceptable excipient, the invented composition optionally can include L-histidine. When L-histidine is included in the composition, the weight ratio of zinc cation to L-histidine is from about 1:5 to about 500:1. When arachidonic acid is included in the composition as described above, the weight ratio of zinc cation to arachidonic acid is from about 1:160 to about 1:10. For all embodiments of the invented composition, the pharmaceutically acceptable excipient can be selected from the group consisting of safflower oil, lecithin, inositol, soybean shortening oil, gelatin, acacia, glycerin, titanium oxide and soybean oil. The composition can be packaged into the form of a capsule which may contain about 0.5 mg to about 50 mg of cyclo-Hispro, and also may contain about 5 mg to about 50 mg of zinc cation.

A second aspect of the invention relates to a composition of matter that includes: (1) purified arachidonic acid; (2)

purified L-histidine; and (3) a pharmaceutically acceptable carrier, wherein the weight ratio of L-histidine to arachidonic acid is from about 1:40 to about 1:1000. In one embodiment, this composition further includes a zinc cation and an anion, wherein the weight ratio of zinc cation to arachidonic acid is from about 1:200 to about 1:2, and the weight ratio of zinc cation to L-histidine is from about 1:5 to about 500:1. In another embodiment, the invented composition further includes cyclo-Hispro. When cyclo-Hispro is present in the composition, the weight ratio of zinc cation to cyclo-Hispro is from about 1:6 to about 5:1. In all embodiments, the anion can be selected from the group consisting of chloride and sulfate. The composition can be packaged in the form of a capsule with each capsule containing from about 0.1 to about 25 mg of L-histidine. Each capsule also can contain from about 100 mg to about 1000 mg of arachidonic acid.

A third aspect of the invention relates to a method of treating a diabetic mammal to alleviate symptoms associated with diabetes. This method includes the step of administering at least once daily to the diabetic mammal a pharmaceutical composition that includes cyclo-Hispro in an amount sufficient to reduce blood glucose concentration. The pharmaceutical composition administered to the mammal optionally can include a zinc cation and an anion, where the amount of zinc cation can range from about 5 to about 50 mg. The amount of cyclo-Hispro present in the administered pharmaceutical composition can range from about 0.5 to about 50 mg, with a more preferred range extending from about 10 to about 30 mg. In another embodiment of the invented method, the pharmaceutical composition administered to the mammal further includes arachidonic acid. When arachidonic acid is administered according to the invented method, it is administered in an amount ranging from about 100 mg to about 1 gram, but alternatively can be administered in an amount ranging from about 500 mg to about 800 mg. According to another embodiment of the invented method, the cyclo-Hispro in the administered composition is present in an amount of 20 mg, and the arachidonic acid is present in an amount of about 200 mg. When the administered composition includes a zinc cation and an anion, the zinc cation can be present in an amount ranging from about 5 mg to about 50 mg. The cyclo-Hispro included in the pharmaceutical composition is present in an amount ranging from about 10 mg to about 30 mg. In a preferred embodiment of the invented method, the pharmaceutical composition is administered orally, and may be administered two to four times daily.

A fourth aspect of the invention relates to another method of treating a diabetic mammal to alleviate symptoms associated with diabetes. This method includes the steps of administering at least once daily to the diabetic mammal a pharmaceutical composition that includes L-histidine in an amount sufficient to reduce blood glucose concentration. In a preferred embodiment, the L-histidine is present in the administered pharmaceutical composition in an amount ranging from about 0.1 to about 25 mg. In another preferred embodiment of the invented method, the administered pharmaceutical composition further includes a zinc cation and an anion. When the administered composition includes a zinc cation and an anion, the zinc cation is present in an amount ranging from about 5 to about 50 mg. According to another preferred embodiment of the invented method, the administered composition includes L-histidine and cyclo-Hispro. In yet another preferred embodiment of the invented method, the pharmaceutical composition which is administered includes L-histidine and arachidonic acid. When arachidonic acid is included in the composition, the arachidonic acid is present in an amount from about 100 mg to about 1000 mg, but may instead be present in an amount ranging from about 500 mg to about 800 mg. Compositions containing arachidonic acid additionally may include a zinc cation, which may be present in an amount ranging from about 5 to about 50 mg. For embodiments of the invented method in which the administered composition includes a zinc cation, the L-histidine included in the pharmaceutical composition is present in an amount ranging from about 0.1 mg to about 1.0 mg. When cyclo-Hispro is included in the administered composition, the cyclo-Hispro is present in an amount ranging from about 10 mg to about 30 mg. In a highly preferred embodiment of the invented method, the administered composition includes L-histidine, arachidonic acid and a zinc salt. In this highly preferred embodiment the zinc cation of the zinc salt is present in an amount ranging from about 5 mg to about 50 mg, the arachidonic acid included in the pharmaceutical composition is present in an amount ranging from about 100 mg to about 1 gram, and the L-histidine included in said pharmaceutical composition is present in an amount ranging from about 0.1 mg to about 1.0 mg. Finally, the pharmaceutical composition can be administered orally, and can be administered two to four times daily.

DETAILED DESCRIPTION OF THE PREFERRED EMBODIMENT

I have discovered that pharmaceutical compositions comprising zinc and either cyclo-Hispro (C-Hispro) or arachidonic acid (AA) are useful for treating diabetes in mammals. My earlier work, disclosed in U.S. Pat. No. 5,411,748 and in the international patent application identified by publication number WO 95/24911 published Sep. 21, 1995, focused on therapeutic compositions that included zinc and a complex organic extract of prostate tissue. Herein, I disclose a composition containing defined chemical species which also can be used for treating diabetes.

Whereas U.S. Pat. No. 5,411,748 disclosed that an organic extract of animal prostate contained materials that could be combined with zinc to result in a therapeutic composition useful for treating diabetes, there was no way to know with certainty what active constituents of the crude extract provided the therapeutic benefit. I reasoned that, since an extract of animal prostate tissue was known to contain substances useful for treating the symptoms of diabetes, and since animal prostate tissue contained high concentrations of zinc, C-Hispro, prostaglandins and L-histidine (L-His), it was possible that one or more of these chemical species contained in the PE may influence the pathophysiology of diabetes. As disclosed below, I have identified an optimal chemical combination of zinc, L-histidine, arachidonic acid and C-Hispro that can be used for controlling blood glucose levels in diabetic animals.

Certain aspects of the present invention regard pharmaceutical compositions. Pharmaceutical compositions according to the present invention contain: (1) a zinc salt, (2) cyclo-Hispro and/or (3) arachidonic acid, and (4) at least one pharmaceutically acceptable excipient. In this invention, these ingredients of the pharmaceutical compositions can be included in "purified" form. By the use of the term "purified", it is intended to mean that these ingredients are in a form enriched relative to the form in which they can be obtained from nature, such as in a prostate extract. The purified ingredients can be obtained either by enriching from a natural source thereof, or by a chemically synthetic method. Thus, the use of the term "purified" does not necessarily imply that these ingredients are completely free, or even substantially free, of other components. Nevertheless, a "purified" ingredient is enriched relative to its concentration in a natural prostate extract.

The pharmaceutical compositions prepared according to the present invention preferably can be packaged in tablet or capsule form by procedures that are well known in the pharmaceutical arts. As referred to herein, numerical values for zinc represent masses or concentrations of the zinc component of a zinc salt. Examples of zinc salts useful in connection with the invention include zinc chloride and zinc sulfate. For treatment of human beings, each tablet or capsule preferably contains about 5 to about 50 mg of zinc, about 0.5 to about 50 mg of cyclo-Hispro, and/or about 100 mg to about 1 gram of arachidonic acid, in addition to the pharmaceutically acceptable excipient or excipients. Thus, a preferred weight ratio of zinc cation to cyclo-Hispro is from about 1:10 to about 100:1, and more preferably is from about 1:6 to about 5:1. When the composition includes arachidonic acid, a preferred weight ratio of zinc cation to arachidonic acid is from about 1:200 to about 1:2, and more preferably is from about 1:160 to about 1:10. It is believed that compositions with these ratios of ingredients are effective in treating a wide range of mammals.

A second composition useful in connection with the invention can also be formulated into a tablet or capsule. For treatment of human beings, tablets or capsules prepared with this second composition each will contain about 5 to about 50 mg of zinc, about 0.1 to about 25 mg of L-histidine, and a pharmaceutically acceptable excipient or excipients. This second composition can optionally include cyclo-Hispro in an amount ranging from about 0.5 mg to about 50 mg, more preferably from about 10 mg to about 30 mg. Another optional ingredient in the second composition would be about 100 mg to about 1 gram of arachidonic acid. Thus, a preferred weight ratio of zinc cation to L-histidine is from about 1:5 to about 500:1. When the second composition includes cyclo-Hispro, a preferred weight ratio of zinc cation to cyclo-Hispro is from about 1:6 to about 5:1, and when the composition includes arachidonic acid, a preferred weight ratio of zinc cation to arachidonic acid is from about 1:200 to about 1:2. It is believed that compositions with these ratios of ingredients are effective in treating a wide range of mammals.

In certain embodiments of the present invention, zinc cation with arachidonic acid alone is effective to relieve the symptoms of diabetes, including a reduction in blood glucose levels. In these embodiments, the amount of zinc cation preferably in a capsule is preferably from about 5 mg to about 50 mg, and the amount of arachidonic acid is approximately 100 mg to 1 gram per capsule which can be administered four times each day. Thus, the preferred ratio of zinc cation to arachidonic acid is approximately 1:2 to about 1:200. Pharmaceutically acceptable carriers, diluents or excipients are also included.

Suitable excipients for tablets and capsules include inert diluents, such as safflower oil, lecithin, inositol, soybean shortening oil, gelatin, acacia, glycerin, titanium oxide and soybean oil. The coating of the capsules can be gelatin or a soluble polymer, as is well understood in the art. The tablets or capsules are suitable for oral administration according to a daily administration regimen.

The pharmaceutical compositions described herein are useful for the treatment of diabetes and other diseases in which zinc or prostaglandin metabolism is impaired. In particular, diabetes can be treated by administering the composition of the present invention to a diabetic mammal in a quantity sufficient to reduce blood glucose concentration in the mammal. Typical doses for patients with diabetes stated as the quantity of zinc, are from about 20 mg to about 80 mg of zinc per day. These doses can be adjusted by one of ordinary skill in the art according to such factors as the weight, age, sex, and state of health of the patient, as well as according to the response to a particular dosage.

The experimental results disclosed herein now identify several defined chemical species which can be combined to result in a composition that is substantially as effective at controlling blood glucose levels in diabetic animals as the combination of zinc and an organic extract of prostate tissue, disclosed in U.S. Pat. No. 5,411,748. Advantageously, the composition disclosed herein can be prepared from readily available chemical species at substantially lower cost and without the trouble or expense associated with preparation of an organic extract of animal tissue. Although the constituents of the invented composition disclosed herein were believed to be present in the prostate extract of the prior art, I have not conducted experiments to verify that this is the case. Accordingly, I have created a new composition useful for treating diabetes. This new composition almost certainly comprises chemical species in amounts and ratios different from any prior art composition of which I am aware.

Two facts that led me to examine the effects of PE on the stimulation of intestinal zinc absorption and clinical manifestations of diabetic rats were that: (1) diabetics exhibit impaired intestinal zinc absorption and low plasma zinc levels, and (2) PE is known to contain agents having a therapeutic effect on the symptoms of diabetic test animals. Presented below are experimental results indicating that prostate extract contained agents that facilitated zinc absorption in diabetic animals. More specifically, the following Example presents results showing that PE could substantially normalize tissue zinc levels in diabetic animals administered with radiolabeled zinc. Indeed, two hours after administering 0.2 mg zinc via intragastric intubation, the average peripheral tissue zinc concentration in streptozotocin-induced diabetic rats was significantly lower than those in normal rats. When 0.2 mg zinc was given together with 2.0 mg PE, the average tissue zinc concentration in diabetic rats was substantially the same as the level measured in non-diabetic rats. Thus, some component of the PE must have promoted more normalized zinc metabolism in the diabetic rats.

Although other materials and methods similar or equivalent to those described herein can be used in the practice or testing of the present invention, the preferred methods and materials are now described.

Example 1 describes the methods used to establish that PE enhanced intestinal zinc absorption and that this enhancement correlated with increased zinc absorption could improve clinical symptoms in rats having steptozotocin-induced diabetes.

EXAMPLE 1

Organic Extract of Animal Prostate Tissue Enhanced Zinc Absorption In Vivo

Animals and Induction of Diabetes

Two month old male Fisher 344 rats (200–250 grams) were obtained from Harlan Industries (Indianapolis, Ind.). After intraperitoneal (i.p.) injection of 200 µL of 50 g/L steptozotocin (Sigma Chemical Co., St. Louis Mo.) in 0.05 mol/L cold citrate buffer solution (pH 4.5), e.g., 45 or 50 mg/kg body weight, rats were kept in metabolic cages for more than three days. Only those rats manifesting hyperglycemia (>11.1 mmol glucose/L blood) were used for experiments. Control rats were injected with citrate buffer. Rats were housed individually and body weight and food and water intakes were monitored regularly. At the end of the experiments animals were killed by injection of 50 mg nembutal/kg body weight (Abbott Laboratories, North Chicago, Ill.), and organs were harvested quickly and stored at −70° C. until analysis.

Preparation of Prostate Extract

Prostate extract was prepared from six month old rabbits obtained from Harlan Industries (Indianapolis, Ind.). Prostates were quickly removed from anesthetized rabbits and frozen at −70° C. The frozen prostates were minced in an aqueous solution adjusted to pH 9.0 with 0.1 mol KOH/L, and homogenized in a POLYTRON homogenizer. Saturated fatty acids were extracted with two volumes of petroleum ether in a separatory funnel for 30 minutes at 4° C., and discarded. The remaining aqueous solution contained the active ingredients, including PG, polyunsaturated fatty acids, testosterone, citric acid, C-Hispro and amino acids. These constituents were extracted using equal volumes of ethyl acetate:isopropyl alcohol: 0.2 mol HCl/L (3:3:1) mixture to the aqueous solution, which separate the organic phase. The organic phase containing active ingredients was evaporated in a freeze drier, and the residual oily material was used for experiments.

Measurement of In Vivo Intestinal Zinc Absorption

After anesthetizing rats by i.p. injection of 50 mg nembutal/kg, each rat was administered via intragastric intubation with either 0.2 mg $^{65}$Zn (Du Pont Company, Wilmington, Del.) (specific activity 3.7×10$^8$ Bq/mg) or the same amount of $^{65}$Zn plus 2.0 mg PE suspended in 2.0 ml distilled water. Exactly two hours later, approximately 0.5 grams of fresh representative samples from each organ were collected in 5 ml polypropylene test tubes. The $^{65}$Zn present in the tubes was measured using a MICROMEDIC gamma counter (ICN Micromedic Systems, Inc., Horsham, Penna.).

Dietary Feeding of Prostate Extract or Other Chemical Constituents

To achieve the same zinc levels in rats as in humans treated with reasonable doses of zinc and PE (800 mg of PE plus 80 mg of zinc per day for a person weighing 75 kg), concentrations of C-Hispro (Sigma Chemical Company, St. Louis, Mo.), AA (Sigma Chemical Company, St. Louis, Mo.) or PE in drinking water were made 100 mg/L plus 10 mg Zn/L based on the fact that diabetic rats drink at least 0.2 mL water/gram body weight/day. The concentration of evening primrose oil (Chemical Company, St. Louis, Mo.), which contains approximately 10% of γ-linolenic acid (an AA precursor) was made 500 mg/L in order to maintain γ-linolenic acid levels close to the AA levels of 100 mg/L.

Measurements of Food and Water Consumption

Food consumption was measured by determining the total weight of food on the previous day minus the weight of the food measured on the next day divided by the rat weight. Similarly, the water consumption was measured by determining the volume of drinking water measured on the previous day minus that of the next day divided by the rat weight.

Analysis of Blood Glucose Concentrations

Glucose concentrations in blood samples were measured using a glucose analyzer purchased from Yellow Spring Instrument Co. (Yellow Spring, Ohio).

Statistical Analysis

Analysis of variance (ANOVA) method was used when determining P-values for multiple test groups. Paired t-test was used for comparison of the results of post-treatment to those of pretreatment. The statistical analysis was carried out using statistical analysis software. A p-value less than 0.05 was considered statistically significant.

The results of the above procedures are summarized in the Tables which follow.

TABLE 1

Changes in Blood Glucose Concentration for Diabetic Rats Consuming Water Containing Various Constituents for Three Weeks

| Drinking Water Contents | n | Glucose Concentrations (mmol glucose/L) | | |
|---|---|---|---|---|
| | | Pre-Treatment | Post-Treatment | Differences |
| (Normal rats) | 6 | 4.71 ± 0.21 | 4.74 ± 0.24 | 0.03 ± 0.12 |
| DW | 11 | 15.39 ± 0.21 | 19.28 ± 1.94* | −3.89 ± 1.53 |
| 10 mg Zn/L | 6 | 14.97 ± 0.21 | 17.71 ± 2.31 | −2.74 ± 2.03 |
| 10 mg Zn plus 500 mg EPO/L | 8 | 14.74 ± 0.21 | 14.72 ± 2.23 | 0.02 ± 0.82# |
| 10 mg Zn plus 100 mg C-Hispro/L | 8 | 16.11 ± 0.21 | 13.08 ± 2.16* | 3.03 ± 1.52## |
| 100 mg PE/L | 7 | 15.66 ± 0.21 | 13.79 ± 2.47 | 1.87 ± 1.00## |
| 10 mg Zn plus 100 mg PE/L | 16 | 17.61 ± 0.21 | 14.16 ± 1.41# | 3.45 ± 1.24### |

All the values are means ± SEM.
n = 6 to 16 per group.
DW distilled water
EPO evening primrose oil
C-Hispro C-Hispro
PE prostate extract
*P<0.05 values of post-treatment compared to those of pre-treatment
**P<0.01 values of post-treatment compared to those of pre-treatment
P<0.05 values compared to those of distilled water
P<0.01 values compared to those of distilled water
P<0.001 values compared to those of distilled water

TABLE 2

Changes in Blood Glucose Concentration for Diabetic Rats Consuming Water Containing Various Constituents for Eighteen Days

| Drinking Water Contents | n | Glucose Concentrations (mmol glucose/L) | | |
|---|---|---|---|---|
| | | Pre-Treatment | Post-Treatment | Differences |
| (Normal rats) | 6 | 4.64 ± 0.14 | | |
| 10 mg Zn/L | 6 | 20.79 ± 2.09 | 20.94 ± 2.41 | 0.15 ± 1.35 |
| 10 mg Zn plus 100 mg AA/L | 6 | 24.20 ± 1.37 | 19.63 ± 0.61 | 4.57 ± 24.4* |
| 10 mg Zn plus 100 mg PE/L | 6 | 27.50 ± 1.37 | 18.97 ± 0.97 | 8.53 ± 0.58* |

Each value is the mean ± SEM of six determinations.
*P<0.05 compared to the values of zinc only.
AA Arachidonic acid
PE Prostate extract

TABLE 3

Changes in Body Weight for Diabetic Rats Consuming Water Containing Various Constituents for Three Weeks

| Drinking Water Contents | n | Body Weights (g) | | |
|---|---|---|---|---|
| | | Pre-Treatment | Post-Treatment | Differences |
| (Normal rats) | 6 | 254.7 ± 5.7 | 315.3 ± 14.3*** | 60.6 ± 2.1 |
| DW | 11 | 255.8 ± 7.9 | 292.3 ± 11.1*** | 36.5 ± 3.8 |

TABLE 3-continued

Changes in Body Weight for Diabetic Rats Consuming Water Containing Various Constituents for Three Weeks

| Drinking Water Contents | n | Body Weights (g) | | |
|---|---|---|---|---|
| | | Pre-Treatment | Post-Treatment | Differences |
| 10 mg Zn/L | 7 | 249.9 ± 4.7 | 281.2 ± 10.6*** | 31.3 ± 6.2 |
| 10 mg Zn plus 500 mg EPO/L | 8 | 266.8 ± 10.2 | 320.6 ± 19.7*** | 53.8 ± 10.3 |
| 10 mg Zn plus 100 mg C-Hispro/L | 8 | 254.5 ± 9.0 | 289.3 ± 11.6** | 34.8 ± 8.3 |
| 100 mg PE/L | 7 | 251.5 ± 5.5 | 280.3 ± 9.6** | 28.8 ± 4.9 |
| 10 mg Zn plus 100 mg PE/L | 16 | 253.6 ± 8.4 | 282.0 ± 10.7* | 28.4 ± 8.6 |

Values are the means (n = 6 to 16) ± SEM.
DW distilled water
EPO evening primrose oil
C-Hispro C-Hispro
PE prostate extract
*$P<0.05$ values of post-treatment compared to those of pre-treatment
**$P<0.01$ values of post-treatment compared to those of pre-treatment
***$P<0.001$ values of post-treatment compared to those of pre-treatment

TABLE 4

Comparison of Body Weights, Food Intake and Water Consumption by Rats Given Plain Drinking Water or Water Containing Either Zinc Alone, or Zinc with PE or AA

| Drinking Water Contents | n | Rat Weights (g) | mg diet/g/d | μl water/g/d |
|---|---|---|---|---|
| (Normal rats) | 6 | 232.3 ± 1.8 | 90.4 ± 2.6 | 213 ± 9 |
| 10 mg Zn/L | 6 | 162.9 ± 8.8 | 215.6 ± 18.4 | 973 ± 59 |
| 10 mg Zn plus 100 mg AA/L | 6 | 169.7 ± 2.8 | 216.6 ± 18.5 | 882 ± 24 |
| 10 mg Zn plus 100 mg AA/L | 6 | 198.8 ± 7.1** | 121.1 ± 10.5** | 398 ± 36*** |

AA arachidonic acid
PE prostate extract
**$P<0.01$ compared to the values of those given zinc only
***$P<0.001$ compared to the values of those given zinc only

TABLE 5

Comparison of Food and Water Consumption by Diabetic Rats Consuming Water Containing Various Constituents for Three Weeks

| Drinking Water Contents | n | mg diet/g/d | μl water/g/d |
|---|---|---|---|
| (Normal rats) | 6 | 96.8 ± 4.3 | 216.3 ± 5.2 |
| DW | 11 | 128.2 ± 5.5 | 460.7 ± 29.8 |
| 10 mg Zn/L | 6 | 148.1 ± 8.0 | 498.0 ± 65.0 |
| 10 mg Zn plus 500 mg EPO/L | 8 | 117.8 ± 9.6 | 515.4 ± 57.7 |
| 10 mg Zn plus 100 mg C-Hispro/L | 8 | 119.1 ± 5.8 | 373.3 ± 47.7* |
| 100 mg PE/L | 7 | 122.8 ± 7.2 | 358.4 ± 58.1* |
| 10 mg Zn plus 100 mg PE/L | 16 | 122.1 ± 5.4 | 334.2 ± 30.4** |

Values are the means (n = 6 to 16) ± SEM.
DW distilled water
C-hispro C-Hispro
EPO evening primrose oil
PE prostate extract
*$P<0.05$ compared to the values of rats fed distilled water
**$P<0.01$ compared to the values of rats fed distilled water The results of the procedures described above showed that diabetic rats administered with PE had tissue zinc levels substantially higher than rats that did not receive PE. When both normal and diabetic rats were given 2.0 mg PE plus 200 μg $^{65}$Zn by intragastric intubation, the mean values of $^{65}$Zn concentrations in blood and organ cells were significantly greater than in animals administered with 200 μg $^{65}$Zn alone. The average value of tissue $^{65}$Zn concentrations in diabetic rats was significantly lower than those in normal rats when given $^{65}$Zn only, as determined by paired t-statistics for the same organs. However, the average tissue $^{65}$Zn concentrations measured in diabetic rats weighing 200 grams given 2.0 mg PE plus 200 μg $^{65}$Zn were similar to the values of normal rats given the same solution containing PE plus $^{65}$Zn.

The results presented in Table 1 showed that differences in the values of blood glucose concentration between pre-treatment and post-treatment in diabetic rats given drinking water containing PE only, zinc plus either PE, C-Hispro or evening primrose oil were significantly greater than those given water containing zinc only or distilled water. The duration of the experiment in this case was three weeks. The values of blood glucose concentration changes in rats given zinc alone did not substantially vary compared to rats given distilled water as a control. Notably, in Table 1 a paired t-test was used to compare pre- and post-treatment, and an ANOVA test was used for comparison between different test groups.

The results presented in Table 2 showed that measurements made for severely diabetic rats (blood glucose concentrations>16.5 mmol/L) provided with drinking water containing either PE plus zinc or AA plus zinc, yielded differences that were more significant than in the trials provided with water containing zinc alone. Notably, the rats that developed blood glucose concentrations higher than 16.5 mM survived more than three weeks without insulin treatment during the experiment.

Although, as indicated in Table 3, all diabetic rats increased their body weights when the diabetic conditions were mild, the group of severely diabetic rats provided with PE plus zinc lost less body weight compared to other groups of rats, as indicated by the results in Table 4. Notably, the weight values presented in Table 4 represent the mean±SEM of the same rat breed after 18 days of consuming water containing the specified constituents. Food and water consumption by rats given PE plus zinc significantly decreased compared to those given water containing only zinc or distilled water, as shown in Tables 4 and 5. In contrast, the group of rats given AA did not maintain low food and water consumption, and high body weight compared to those given zinc only (Table 4). Only the blood glucose concentrations in these rats were lower than in rats given zinc alone (Table 3). Table 5 showed that when rats were mildly diabetic, water consumption by the rats given either PE only or C-Hispro plus zinc also decreased compared to rats given distilled water only.

Since PE markedly enhanced intestinal zinc absorption in control and diabetic rats, PE in combination with zinc can lower blood glucose levels (Tables 1 and 2) and ameliorate diabetic symptoms (Tables 3–5) by stimulating intestinal zinc absorption. Earlier studies indicated that hepatic glucose output increased more than five fold in the streptozotocin-induced diabetic rats under the same plasma insulin concentrations (Burcelin et al., *Diabetologia* 38:283 (1995)). Thus, relatively high blood glucose may be maintained in the streptozotocin-induced diabetic rats (Tables 1 and 2) even though the symptoms associated with diabetes were improved (Tables 4 & 5).

Zinc in combination with AA or C-Hispro also lowered blood glucose levels (Tables 1 & 2) and improved diabetic manifestations (Tables 3–5). Since these factors are also involved in the regulation of zinc metabolism, stimulation of intestinal zinc absorption and zinc uptake by these agents in peripheral tissues may be the cause of improved diabetic manifestations. However, these factors alone may not be as effective as PE that contains essentially all the constituents involved in the regulation of zinc metabolism.

The results disclosed hereinabove demonstrated that blood glucose concentrations in diabetic animals administered with a composition comprising zinc and either C-Hispro or AA advantageously were substantially lower than in diabetic animals administered with zinc alone. Moreover, the results indicated that the combination of zinc and C-Hispro reduced blood glucose concentrations substantially as effectively as the combination of zinc and prostate extract. The results presented below confirm that compositions which included zinc and C-Hispro were useful for treating the symptoms associated with diabetes, and additionally confirmed that compositions including zinc and AA could be used for the same purpose.

Interestingly, C-Hispro is a major thyrotropin releasing hormone (TRH) metabolite having a strong zinc chelating capacity, and also is present in greater amounts in the prostate than in any other tissue (Pekary et al., *Peptides* 14:315 (1993)). Accordingly, I also expect that thyrotropin releasing hormone will be useful for treating diabetes. Based on the fact that these constituents are all essential for intestinal zinc absorption, these constituents may improve zinc uptake rates in the tissues of diabetic animals, and in turn ameliorate diabetic manifestations.

Example 2 describes the methods used to establish a new chemical composition useful for treating the symptoms associated with diabetes. These methods also were used to establish the optimal dosages of C-Hispro and AA useful for improving diabetic symptoms.

EXAMPLE 2

Identifying Active Agents for Treating Diabetes and Optimizing Dosages

Rats were first made diabetic by injection with streptozotocin, and then allowed to stabilize for a period of two weeks. During this stabilization period, a few of the test animals died. After the two week period, the surviving diabetic rats were divided into seven groups and provided either with plain drinking water as a control, or drinking water containing one of six compositions to be tested for their effects on various parameters associated with the diabetic condition. Constituents included in these compositions, in varying combinations, were: zinc (20 mg/L); L-histidine (20 mg/L); arachidonic acid (100 mg/L); testosterone (100 mg/L); and C-Hispro (10 mg/L).

Diabetic rats receiving one of the six test compositions or control drinking water were monitored for blood glucose concentration, body weight and water consumption over a period of about one month. Values for these parameters were plotted on a graph, and a regression line drawn. Since some of the compositions dramatically improved the measured parameters in a period of only a few days, a regression line was plotted only for the data points spanning the period during which change in the measured value occurred. Thus, if the blood glucose concentration increased substantially steadily over the course of the experiment, the slope of the regression line was reported along with the number of days duration during which the change was monitored. If a change in the measured parameter took place during the first day of treatment and showed no change thereafter, a quantitative result was reported as having a duration of only one day. This approach allowed for monitoring both the physiological effect of the test composition as well as assessing the rapidity of the effect, and was followed consistently in reporting the data in Tables 6–8.

TABLE 6

Blood Glucose Concentration Changes During Dietary Feeding of Defined Chemical Species in the Drinking Water

| | Test Composition | Blood Glucose Changes | Days Duration |
|---|---|---|---|
| 1. | Distilled water | 1.96 mg glucose/dL/day | 29 days |
| 2. | Zinc only | 1.51 mg glucose/dL/day | 26 days |
| 3. | Zinc plus L-His | 3.92 mg glucose/dL/day | 28 days |
| 4. | Zinc plus L-His testosterone | 4.20 mg glucose/dL/day | 30 days |
| 5. | Zinc plus L-His arachidonic acid | −35.9 mg glucose/dL/day | 5 days |
| 6. | Zinc plus L-His C-hispro | −209 mg glucose/dL/day | 1 day |
| 7. | Zinc plus L-His C-Hispro, arachidonic acid, and testosterone | −69.5 mg glucose/dL/day | 2 days |

Concentrations of chemicals were: 20 mg zinc; 20 mg L-histidine; 100 mg arachidonic acid; 100 mg testosterone; and 10 mg C-Hispro/L.

The results presented in Table 6 show that diabetic rats administered with water containing zinc in combination with either C-Hispro or arachidonic acid advantageously exhibited significantly decreased blood glucose concentrations. The most dramatic reductions in blood glucose concentration were achieved when diabetic rats were provided with water that included zinc, L-His and C-Hispro. In this instance, blood glucose was reduced by 209 mg glucose/dL/day in the first day of treatment. After the first day of treatment, glucose levels in this group fluctuated somewhat, but remained substantially constant. A composition that included zinc, L-His, C-Hispro, AA and testosterone reduced blood glucose by 69.5 mg glucose/dL/day within two days of treatment. A composition that included zinc, L-His and AA also was effective at reducing blood glucose, but required five days to realize the full beneficial effect of the treatment.

Thus, the results presented in Table 6 confirmed the earlier finding that compositions that included zinc and C-Hispro could be used to improve the symptoms associated with diabetes. The results additionally indicated that compositions that included zinc and AA also could be used as a therapeutic composition. There was no apparent benefit when testosterone was included in the composition. Comparing these findings with those presented under Example 1 suggested that L-His was not a required component of a therapeutic composition useful for treating diabetes. Accordingly, the minimal composition useful for treating symptoms associated with diabetes included zinc and C-Hispro and/or AA.

TABLE 7

Growth Rates of Diabetic Rats During Administration with Various Chemicals Dissolved in Drinking Water

| | Test Composition | Body Weight Changes | Days Duration |
|---|---|---|---|
| 1. | Distilled water | 1.51 g/day | 30 days |
| 2. | Zinc only | 2.87 g/day | 30 days |
| 3. | Zinc plus L-His | 2.68 g/day | 30 days |
| 4. | Zinc plus L-His testosterone | 3.32 g/day | 30 days |
| 5. | Zinc plus L-His arachidonic acid | 2.95 g/day | 30 days |
| 6. | Zinc plus L-His C-Hispro | 5.00 g/day | 30 days |

TABLE 7-continued

Growth Rates of Diabetic Rats During Administration with
Various Chemicals Dissolved in Drinking Water

| | Test Composition | Body Weight Changes | Days Duration |
|---|---|---|---|
| 7. | Zinc plus L-His C-Hispro, arachidonic acid, and testosterone | 5.25 g/day | 30 days |

Zinc concentration was 20 mg/L; L-histidine concentration was 20 mg/L; arachidonic acid concentration was 100 mg/L; testosterone concentration was 100 mg/L; C-Hispro concentration was 10 mg/L.

plus L-His, C-Hispro, arachidonic acid and testosterone advantageously showed the greatest weight gains. In this measurement, the rats receiving zinc plus L-His and AA showed comparatively less dramatic weight gains, even though this group showed improved blood glucose readings. These results confirmed that diabetic animals administered with compositions that included zinc and C-Hispro showed the greatest improvement in diabetic symptoms.

TABLE 8

Water Consumption by Diabetic Rats During Administration with
Various Chemicals Dissolved in Drinking Water

| | Test Composition | Water Consumption | Days Duration |
|---|---|---|---|
| 1. | Distilled water | 1.238 ± 0.123 ml/g/day | 20 days |
| 2. | Zinc only | 0.825 ± 0.055 ml/g/day | 20 days |
| 3. | Zinc plus L-His | 1.083 ± 0.030 ml/g/day | 20 days |
| 4. | Zinc plus L-His testosterone | 0.870 ± 0.052 ml/g/day | 20 days |
| 5. | Zinc plus L-His arachidonic acid | 0.605 ± 0.030 ml/g/day | 20 days |
| 6. | Zinc plus L-His C-Hispro | 0.453 ± 0.033 ml/g/day | 20 days |
| 7. | Zinc plus L-His C-Hispro, arachidonic acid, and testosterone | 0.937 ± 0.059 ml/g/day | 20 days |

Zinc concentration was 20 mg/L; L-histidine concentration was 20 mg/L; arachidonic acid concentration was 100 mg/L; testosterone concentration was 100 mg/L; C-Hispro concentration was 10 mg/L.

The results presented in Table 8 showed that water consumption by diabetic rats receiving C-Hispro was lower than in the other groups tested. This was consistent with a reduction of the excessive thirst that is known to characterize diabetes. Notably, the second lowest water consumption was measured in the group of rats administered with zinc plus L-His and AA. This confirmed that another of the symptoms associated with diabetes, excessive thirst, was controlled by compositions that included zinc and C-Hispro and/or arachidonic acid. Again, based on the results presented under Example 1, L-His was not a required constituent of the therapeutic composition.

TABLE 9

Optimizing the Level of C-Hispro Intake for
Improving Diabetes (Unrestricted Water Intake)

| Range of C-Hispro intake | Mean mg glucose/dL before Tmt | Mean mg glucose/dL after Tmt | Changes of mg glucose/dL |
|---|---|---|---|
| 281 to 290 µg/kg | 373 ± 30 | 258 ± 27 | 115 ± 33 |
| 386 to 466 µg/kg | 411 ± 22 | 353 ± 37 | 58 ± 47 |

TABLE 9-continued

Optimizing the Level of C-Hispro Intake for
Improving Diabetes (Unrestricted Water Intake)

| Range of C-Hispro intake | Mean mg glucose/dL before Tmt | Mean mg glucose/dL after Tmt | Changes of mg glucose/dL |
|---|---|---|---|
| 452 to 554 µg/kg | 417 ± 8 | 367 ± 47 | 50 ± 41 |
| 569 to 680 µg/kg | 359 ± 46 | 314 ± 20 | 45 ± 16 |

10 mg Zn/L was included in the drinking water.

TABLE 10

Optimizing the Level of C-Hispro Intake for
Improving Diabetes (Restricted Water Intake)

| Range of C-Hispro intake | Mean mg glucose/dL before Tmt | Mean mg glucose/dL after Tmt | Changes of mg glucose/dL |
|---|---|---|---|
| 217 to 231 µg/kg | 372 ± 33 | 213 ± 43 | 159 ± 45 |
| 303 to 337 µg/kg | 422 ± 27 | 192 ± 28 | 230 ± 14 |
| 448 to 463 µg/kg | 342 ± 20 | 216 ± 23 | 126 ± 34 |
| 554 to 597 µg/kg | 314 ± 24 | 221 ± 12 | 93 ± 32 |

10 mg Zn/L was included in the drinking water.

The results presented in Table 9 were used to determine the optimal concentration of C-Hispro useful for improving the symptoms associated with diabetes. Since rats consuming water containing C-Hispro ad libitum also consumed the lowest water volume as evidenced by the results in Table 8, the optimal concentration of C-Hispro for improving the symptoms of diabetes was determined by providing animals with water containing different concentrations of c-Hispro. The amounts of consumed were determined by measuring the amount of water consumed, dividing this value by the weight of the rat and multiplying the result by the c-Hispro concentration. The amount of C-Hispro intake for the most dramatic improvement of symptoms of diabetes was about 300 µg/kg/day, based on the results presented in Tables 9 and 10. When taken together, the results presented in Tables 9 and 10 indicated that the most effective range of C-Hispro for improving the symptoms of diabetes was from about 300 to about 340 µg/kg, but a therapeutic effect also was observed for the range of from about 200 µg/kg to about 600 µg/kg. Similar ranges of dosages also are expected to be useful for treating diabetic mammals, including humans.

TABLE 11

Blood Glucose Concentrations in Diabetic Rats Administered
with Arachidonic Acid and 0.5 mg/kg/day of L-Histidine

| Dose of arachidonic acid | mg glu/dL Pre-Treatment | mg glu/dL Post-Treatment | mg glu/dL improvement |
|---|---|---|---|
| 0 mg/kg/day | 204 ± 22 | 304 ± 50 | −100 ± 62 |
| 2.02 to 2.39 mg/kg/day | 263 ± 48 | 321 ± 34 | −58 ± 16 |
| 3.04 to 3.58 mg/kg/day | 303 ± 23 | 256 ± 25 | 47 ± 26 |
| 4.05 to 4.78 mg/kg/day | 308 ± 17 | 247 ± 32 | 61 ± 43 |
| 5.06 to 5.97 mg/kg/day | 426 ± 56 | 252 ± 29 | 174 ± 53 |
| 10.12 to 11.95 mg/kg/day | 393 ± 23 | 187 ± 15 | 206 ± 25 |
| 15.18 to 17.91 mg/kg/day | 368 ± 25 | 184 ± 16 | 184 ± 30 |
| 20.24 to 23.88 mg/kg/day | 379 ± 25 | 241 ± 18 | 138 ± 33 |
| 25.30 to 29.85 mg/kg/day | 443 ± 52 | 301 ± 27 | 142 ± 66 |

Table 11 shows that the optimal amount of AA for improving the symptoms of diabetes in rats was about 10 mg/kg/day, and 0.5 mg/kg concentrations of L-histidine in the drinking water improved diabetes. In the experiment used to produce the results presented in Table 11, the concentration of AA was varied and the L-histidine concentration was held constant. Thus, a range of from 3–30 mg/kg/day of AA provided a therapeutic benefit, with a range of from 10–12 mg/kg/day of AA providing the greatest benefit.

The results presented above indicated that oral administration with a composition comprising zinc in an amount preferably ranging from about 5 mg to about 50 mg, together with C-Hispro in an amount preferably ranging from about 0.5 to 50 mg, and/or arachidonic acid in an amount preferably ranging from about 100 mg to about 1 gram could be used to alleviate the symptoms associated with diabetes. Even more preferred dosages for C-Hispro range from about 10 to about 30 mg, while even more preferred dosages for arachidonic acid range from 500 to 800 mg. All of these values correspond to daily dosages. Since the invented composition can be administered each day as several small dosages, the daily dosage value can be divided among these several smaller dosages. For example, if the daily dosage of one of the compositions disclosed herein is administered in the form of four tablets, then each tablet will contain one-fourth of the stated daily dosage.

The most preferred dietary supplement for improving the symptoms of diabetes contains about 10 mg zinc, about 200 mg arachidonic acid, about 20 mg C-Hispro and about 0.5 mg L-histidine. This therapeutic composition can be taken orally four times a day. Thus, the amount of zinc in the composition can be between about 0 and about 20 mg, the amount of AA can be between about 0 and about 300 mg, the amount of C-Hispro can be between about 0 and about 30 mg, and the amount of L-His can be between about 0 and about 0.5 mg.

Because C-Hispro is a metabolite of thyrotrophin releasing hormone (TRH) I also expect that TRH will be useful in a therapeutic composition for treating diabetes.

What is claimed is:

1. A composition to treat a diabetic mammal, comprising:
 a zinc salt comprising a zinc cation and an anion;
 purified cyclo-Hispro; and
 a pharmaceutically acceptable excipient,
wherein the weight ratio of zinc cation to cyclo-Hispro is from about 1:10 to about 100:1.

2. The composition of claim 1, wherein the weight ratio of zinc cation to cyclo-Hispro is from about 1:6 to about 5:1.

3. The composition of claim 1, wherein the anion is selected from the group consisting of chloride and sulfate.

4. The composition of claim 1, further comprising arachidonic acid.

5. The composition of claim 4, wherein the weight ratio of zinc cation to arachidonic acid is from about 1:200 to about 1:2.

6. The composition of claim 1, further comprising L-histidine.

7. The composition of claim 6, wherein the weight ratio of zinc cation to L-histidine is from about 1:5 to about 500:1.

8. The composition of claim 5, wherein the weight ratio of zinc cation to arachidonic acid is from about 1:160 to about 1:10.

9. The composition of claim 1, wherein the pharmaceutically acceptable excipient is selected from the group consisting of safflower oil, lecithin, inositol, soybean shortening oil, gelatin, acacia, glycerin, titanium oxide and soybean oil.

10. The composition of claim 1, wherein said composition is in the form of a capsule.

11. The composition of claim 10, wherein each capsule contains about 0.5 mg to about 50 mg of cyclo-Hispro.

12. The composition of claim 10, wherein each capsule contains about 5 mg to about 50 mg of zinc cation.

13. A method of treating a diabetic mammal to alleviate symptoms associated with diabetes, said method comprising administering at least once daily to the diabetic mammal a pharmaceutical composition in an amount sufficient to reduce blood glucose concentration, said pharmaceutical composition comprising
 a zinc salt comprising a zinc cation and an anion;
 purified cyclo-Hispro; and
 a pharmaceutically acceptable excipient,
wherein the weight ratio of zinc cation to cyclo-Hispro is from about 1:10 to about 100:1.

14. The method of claim 13, wherein the zinc cation is present in the administered pharmaceutical composition in an amount ranging from about 5 to about 50 mg.

15. The method of claim 13, wherein the cyclo-Hispro is present in the administered pharmaceutical composition in an amount ranging from about 0.5 to about 50 mg.

16. The method of claim 15, wherein the cyclo-Hispro is present in the administered pharmaceutical composition in an amount ranging from about 10 to about 30 mg.

17. The method of claim 13, wherein the pharmaceutical composition administered further comprises arachidonic acid.

18. The method of claim 17, wherein the arachidonic acid is administered to said mammal in an amount ranging from about 100 mg to about 1 gram.

19. The method of claim 18, wherein the arachidonic acid is administered to the mammal in an amount ranging from about 500 mg to about 800 mg.

20. The method of claim 17, wherein the cyclo-Hispro is present in an amount of 20 mg, and the arachidonic acid is present in an amount of about 200 mg.

21. The method of claim 13, wherein the zinc cation included in said pharmaceutical composition is present in an amount ranging from about 5 mg to about 50 mg, and wherein the cyclo-Hispro included in said pharmaceutical composition is present in an amount ranging from about 10 mg to about 30 mg.

22. The method of claim 13, wherein the pharmaceutical composition is administered orally.

23. The method of claim 13, wherein the pharmaceutical administration is administered two to four times daily.

* * * * *